United States Patent [19]

Landauer et al.

[11] 4,306,102
[45] Dec. 15, 1981

[54] P-TERT.BUTYLBENZOTRIBROMIDE AND P-TERT.BUTYLBENZOYL BROMIDE AND PROCESS FOR THEIR MANUFACTURE

[75] Inventors: Franz Landauer, Frankfurt am Main; Georg Schaeffer, Hofheim am Taunus, both of Fed. Rep. of Germany

[73] Assignee: Hoechst Aktiengesellschaft, Frankfurt am Main, Fed. Rep. of Germany

[21] Appl. No.: 94,179

[22] Filed: Nov. 14, 1979

[30] Foreign Application Priority Data

Nov. 16, 1978 [DE] Fed. Rep. of Germany ....... 2849663

[51] Int. Cl.$^3$ .................. C07C 17/14; C07C 21/24; C07C 57/72
[52] U.S. Cl. .................. 570/185; 207/158 HA; 260/544 D; 570/196; 570/127
[58] Field of Search ................... 260/651 R, 544 D; 570/185, 127

[56] References Cited

U.S. PATENT DOCUMENTS

| | | | |
|---|---|---|---|
| 3,869,489 | 3/1975 | Tiquert et al. | 260/453 |
| 4,110,373 | 8/1978 | Day | 26/543 |

*Primary Examiner*—Robert Gerstl
*Attorney, Agent, or Firm*—Curtis, Morris & Safford

[57] ABSTRACT p-Tert.butylbenzotribromide and the derivatives thereof which is halogen-substituted at the nucleus are prepared under side chain halogenation conditions by bromination of p-tert.butyltoluene and its derivatives substituted at the nucleus by halogen. Practically no undesired bromination in the nucleus or at the tert.butyl radical takes place.

By partial saponification of the benzotribromide the corresponding benzoyl bromide is obtained. Further saponification of the latter or complete saponification of the benzotribromide yields p-tert.butylbenzoic acid and derivatives thereof which are halogen substituted at the nucleus, the esters of which can be used in pharmacology.

3 Claims, No Drawings

P-TERT.BUTYLBENZOTRIBROMIDE AND P-TERT.BUTYLBENZOYL BROMIDE AND PROCESS FOR THEIR MANUFACTURE

This invention relates to p-tert.butylbenzotribromide and p-tert.butylbenzoyl bromide, to derivatives thereof which are halogen-substituted at the nucleus and to a process for their manufacture.

p-tert.Butylbenzotribromide and p-tert.butylbenzoyl bromide and their derivatives substituted at the nucleus by halogen atoms are valuable and novel intermediates for the manufacture of p-tert.butylbenzoic acid and their derivatives optionally substituted by halogen at the nucleus. The esters have, in part, spasmolytic and, in part, even fungicidal properties and, therefore, they can be used in pharmacology. Up to now, p-tert.butylbenzoic acid has mainly been prepared by the Grignard process from p-tert.butyl-phenyl-magnesium bromide and $CO_2$ or by heating p-tert.butylbenzyl bromide or 1-isopropyl-4-tert.butylbenzene with nitric acid (cf. Beilstein, E III 9 -System no. 944/H 560, pages 2525 and 2526). These processes have disadvantages, especially as regards technology. The Grignard synthesis is very expensive when carried out on an industrial scale and the oxidation with nitric acid requires expensive apparatus for the control of contamination of sewage and air.

As ascertained by our own experiments, the use of another method known for the manufacture of aromatic acids, namely the saponification of benzotrichlorides with water, for the manufacture of p-tert.butylbenzoic acid proved to be of little use since chlorination by means of free radicals of p-tert.butyltoluene to produce the necessary p-tert.-butyl benzotrichloride yields products the organically bound chlorine atoms of which can be split off only partially under the usual conditions of alkaline hydrolysis (cf. Houben-Weyl, Methoden der organischen Chemie, volume II, page 233, Stuttgard 1953), which fact points to a rather substantial chlorination of the nucleus. Such a reaction is, of course, not desired when, ultimately, pure p-tert.-butylbenzoic acid or its corresponding derivatives are wanted. In some cases derivatives of p-tert.butylbenzoic acid substituted at the nucleus by chlorine are required for the manufacture of pharmaceutical agents, but in the chlorination of p-tert.butyltoluene the chlorine is often substituted into a nuclear position at which chlorine-substitution is undesirable. And in many cases, no substitution at the nucleus by chlorine is wanted, for example if the nucleus is already substituted by other halogen atoms (F, Br, I), and a further substitution by chlorine should not take place.

In the endeavour to find a more favorable and more economical synthesis of p-tert.butylbenzoic acid and especially of an acid halide and derivatives thereof substituted by halogen at the nucleus, it has been found that the novel intermediate p-tert.butylbenzotribromide and its derivatives substituted by halogen at the nucleus make such a synthesis possible.

It is, therefore, an object of the present invention to provide p-tert.butylbenzotribromide and its derivatives substituted by halogen at the nucleus of the following formula I

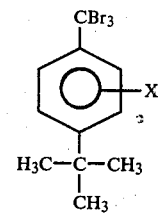

(I)

as ell as p-tert.butylbenzoyl bromide and its derivatives substituted by halogen at the nucleus of the following formula II

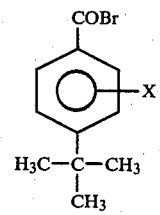

(II)

In the two formulae X denotes H, F, Cl, Br or I, preferably H, F, Cl or Br, and more preferably H.

Hence, compounds of the formula I are

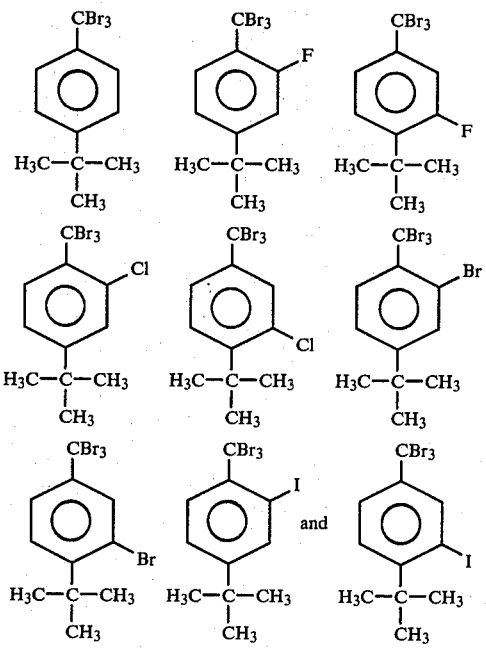

and compounds of the formula II are

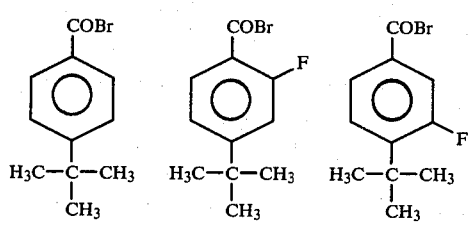

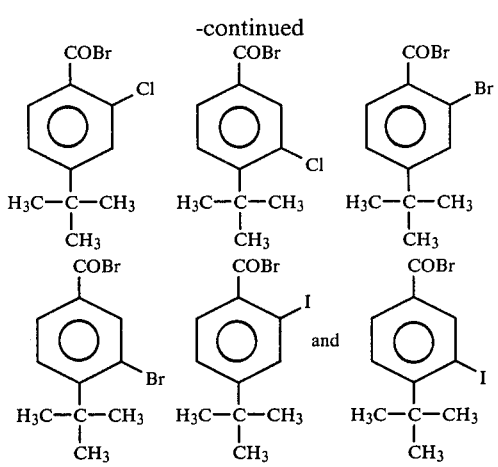

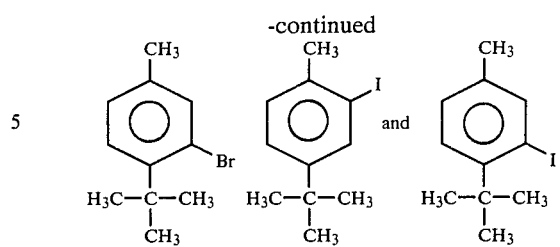

It is another object of the invention to provide a process for the manufacture of p-tert.butylbenzotribromide and p-tert.butylbenzoyl bromide and their derivatives substituted by halogen at the nucleus, which comprises (a) reacting p-tert.butyl toluene and its derivatives substituted at the nucleus by halogen with about 3 mols of bromine per mol of hydrocarbon, at a temperature of from about 40° to 200° C., preferably about 80° to 160° C., optionally under the action of high energy radiation or in the presence of radical-forming agents and, (b) saponifying the p-tert.butylbenzotribromide and its derivatives substituted at the nucleus by halogen, optionally after their isolation at elevated temperature, with about 1 mol of water for each mol of tribromide formed, optionally in the presence of the usual saponification catalysts, to give p-tert.butylbenzoyl bromide and its derivatives substituted at the nucleus by halogen.

Suitable starting materials to be used in the process of the invention are p-tert.butyltoluene and its derivatives unsubstituted or substituted at the nucleus by one or several halogen atoms (F, Cl, Br, I). When the reaction is complete, the final product carries, of course, the same substituents at the nucleus as the starting compound. Besides p-tert.butyltoluene unsubstituted at the nucleus, there are preferred as starting compounds those derivatives the nucleus of which is substituted by one halogen atom only, namely

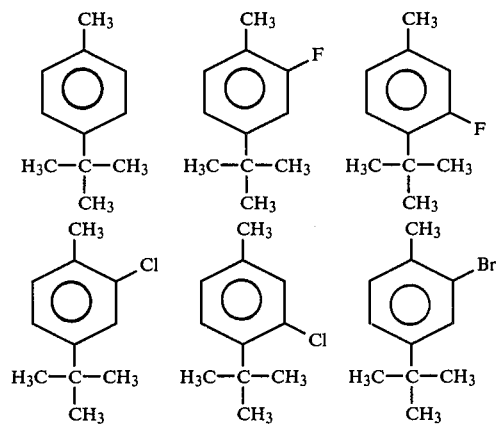

From among the substituted derivatives those having F, Cl and Br substituents are preferred. The compounds of formulae I and II are obtained by using as starting compounds p-tert.butyltoluene which is unsubstituted at the nucleus or is substituted by one halogen atom at the nucleus.

To carry out the process of the invention, the starting compound used is reacted with about 3 (2.8–3.2) mols of bromine per mol of starting compound at the indicated temperatures, approximately 40° to 200° C., preferably 80° to 160° C., optionally under the action of high energy radiation or in the presence of radical forming agents. As high energy radiation ultraviolet light is preferably used.

Suitable radical-forming agents are organic peroxides and azoisobutyronitrile as generally used in chlorination reactions of side chains.

High energy radiation or the presence of radical-forming agent is not absolutely necessary for the success of the reaction, but they greatly accelerate same and, therefore, they have an advantageous effect.

The bromine can be added dropwise in liquid form or introduced in gaseous form after evaporation. In the latter case an inert gas, for example $N_2$ or argon, may be added. The bromination can be carried out without as well as with a suitable solvent, such as, for example and inert hydrocarbon, preferably a halogenated hydrocarbon, for example carbon tetrachloride or o-dichlorobenzene. The reaction can be carried out with or without application of pressure, discontinuously as well as continuously, in suitable apparatus.

p-tert.Butylbenzotribromide and its derivatives substituted by halogen at the nucleus which are obtained from correspondingly substituted derivatives of p-tert.butyltoluene do not have undesired bromine substituents at the aromatic nucleus and constitute novel compounds.

For the preparation of the corresponding benzoyl bromide therefrom they can be isolated and purified, for example by recrystallization, and saponified or they can be saponified without previous isolation. The saponification is carried out by any method known for the saponification of benzotrihalides to give the corresponding benzoyl halides at elevated temperature, preferably at about 80° to 200° C., more preferably about 90° to 150° C., with an equivalent amount of water (approximately 1 mol per mol of tribromide), optionally in the presence of the usual saponification catalysts, for example metal halides such as $FeCl_3$, $FeBr_3$ and $ZnCl_2$, or also $H_2SO_4$, and the like. By adding water in an amount exceeding the calculated equivalent amount, it is also possible, of course, to proceed with the saponification until the corresponding benzoic acid is obtained. The saponification can be carried out at atmospheric pressure as well as under elevated pressure. Inert solvents may also be added, for example hydrocarbons or chlorohydrocarbons. The use of emulsifiers, which ensure a good mixing of the organic phase with the water added, is also possible.

To prepare the acid bromide from the corresponding benzotribromide, the latter can also be reacted with another carboxylic acid in the presence of, for example, catalytic amounts of $ZnCl_2$ at elevated temperature. In this reaction the acid bromide of the carboxylic acid added is formed in addition to p-tert.butylbenzoyl bromide.

The hydrogen bromide formed in the process of the invention is preferably absorbed in a conventional absorption device. It can be directly used for other chemical reactions or it can be sold.

In the process of the invention p-tert.butylbenzotribromide and p-tert.butylbenzoyl bromide and the derivatives thereof substituted by halogen at the nucleus are obtained in excellent yields. Besides the substituents at the nucleus present in the starting products they do not carry other undesired bromine substituents, which fact is extremely surprising as halogenations with chlorine and bromine normally take an identical course and, as a result of a side chain chlorination of p-tert.butyltoluene, a considerable chlorination at the nucleus cannot be avoided. In contradistinction thereto, in the bromination of p-tert.-butyltoluene and of the corresponding substitution product thereof no or substantially no undesired halogenation at the nucleus and no bromination of the tert.butyl group take place.

The high selectivity and yield obtained by the process of the invention and the fact that, compared with some processes of the state of the art, no special purification of the waste water is required, represent a considerable advancement.

The invention will now be described in further detail by the following example which is followed by a comparative example in which, instead of bromine, chlorine is used as halogenation agent for p-tert.butyltoluene.

EXAMPLE according to the invention (a) p-tert.butylbenzotribromide

In a 1 liter, four-necked flask provided with stirrer, thermometer, dropping funnel and reflux condenser, which flask was connected with an absorption device filled with water for hydrogen bromide, 480 g (3 mols) of bromine were added dropwise during the course of 6 to 7 hours, at 110° to 120° C. and while irradiating with ultraviolet light, to 148 g (1 mol) of p-tert.butyltoluene. After addition of approximately two thirds of the bromine, the temperature was raised to 145° to 155° C.

After addition of the total amount of bromine, stirring of the mixture was continued for a further 15 to 20 minutes. Next, the residual hydrogen bromide was blown out with nitrogen.

Yield of crude product 378 g (98.2% of theory).

The crude product was recrystallized from isopropanol. It then melted at 118° to 119° C.

Analysis: total bromine 62.6%; saponifiable bromine 62.1% (saponification with alcoholic KOH and argentometric determination of the ionogenic bromine).

Calculated saponifiable bromine 62.3%; 236 g (2.92 mols) of hydrogen bromide were found, i.e. 97.3% of the theory.

(b) p-tert.butylbenzoylbromide

In a flask provided with stirrer, thermometer, dosing pump and reflux condenser and connected with an absorption device for hydrogen bromide a solution of 0.8 g of ferric chloride in 4 g of $H_2O$ was added within 5 minutes and by means of a small dosing pump to 770 g of p-tert.butylbenzotribromide (2 mols) at a temperature of 110° to 120° C. During the course of 1.5 hours 32 g of water were then uniformly pumped in.

The hydrogen bromide set free was taken up in water. 319 g thereof, i.e. 98.5% of the theory, were found.

The yield of crude p-tert.butylbenzoylbromide amouned to 465 g, which was 96.5% of the theory.

The acid bromide was purified by vacuum distillation. It had a boiling point of 96° to 98° C. under 0.16 mm Hg.

|  | Analysis | Calculated | Found |
|---|---|---|---|
|  | C | 54.7% | 54.4% |
|  | H | 5.4% | 5.5% |
| saponified | Br | 33.2% | 33.6% |

COMPARATIVE EXAMPLE

In the apparatus and under the conditions of the preceding example, 296 g of p-tert.butyltoluene (2 mols) were chlorinated by introducing 284 g (about 4.1 mols) of chlorine over a period of 3.5 hours. After blowing out the hydrogen chloride, 415 g of crude product were obtained, which was analyzed as follows:

Total chlorine: 31.5% saponifiable chlorine: 20.85% (saponification with alcoholic KOH and argentometric determination of ionogenic chlorine)

from which it was calculated that 10.20% of chlorine was bound to the nucleus and not capable of being split off.

Hence, about one third of the total, organically bound chlorine was useless for the saponification, in this case to p-tert.butylbenzaldehyde.

The comparative example was carried out only with the amount of chlorine necessary for the preparation of the benzal stage (—$CHCl_2$). Obviously, a considerable chlorination at the nucleus had taken place. If the chlorination had been carried out with the higher amount of chlorine as required for the manufacture of the benzotrichloride stage (—$CCl_2$), an decreased chlorination at the nucleus could not have been expected.

Using sulfuryl chloride instead of chlorine in the comparative example gave a very similar result.

What is claimed is:

1. A compound selected from the group consisting of p-tert.butylbenzotribromide and its derivatives substituted by halogen at the nucleus of the formula

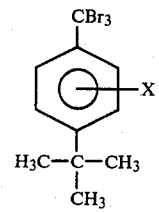

in which X is H, F, Cl, Br or I.

2. A compound as defined in claim 1 wherein X is H, F, Cl or Br.

3. A compound as defined in claim 2, wherein X is H.

* * * * *